(12) United States Patent
Jarvi et al.

(10) Patent No.: US 6,399,829 B1
(45) Date of Patent: Jun. 4, 2002

(54) **SYNTHESIS AND PURIFICATION OF (R*, R*)-2-[ (DIMETHYLAMINO) METHYL]-1-(3-METHOXYPHENYL) CYCLOHEXANOL HYDROCHLORIDE**

(75) Inventors: Esa T. Jarvi, Ballwin; Neile A. Grayson, Glendale, both of MO (US); Robert E. Halvachs, Belleville, IL (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/700,889
(22) PCT Filed: May 20, 1999
(86) PCT No.: PCT/US99/11336
§ 371 (c)(1), (2), (4) Date: Nov. 20, 2000
(87) PCT Pub. No.: WO99/61405
PCT Pub. Date: Dec. 2, 1999

Related U.S. Application Data

(60) Provisional application No. 60/086,498, filed on May 22, 1998.

(51) Int. Cl.[7] .............................................. C07C 209/00
(52) U.S. Cl. ........................ 564/425; 564/424; 564/303; 564/304; 564/438
(58) Field of Search ................................ 564/303, 304, 564/438, 424; 504/425

(56) References Cited

U.S. PATENT DOCUMENTS 3,652,589 A * 3/1972 Flick et al.
5,414,129 A * 5/1995 Cherkez et al.

FOREIGN PATENT DOCUMENTS

EP    0778262    * 11/1997

* cited by examiner

*Primary Examiner*—Samuel Barts

(57) ABSTRACT

(R*,R*)-2-[(dimethylamino)methyl]-1-(3-methoxyphenyl) cyclohexanol (Tramadol) is synthesized in a Grignard reaction in the presence of an additive resulting in a higher trans:cis ratio of product than is obtained in the absence of the additive. The Grignard reaction between 3 bromoanisole and the appropriate Mannich base in the presence of an amine or ether additive gives the amine product in an improved trans/cis ratio. The base is converted to its hydrochloride and recrystallized from a low molecular weight nitrile such as acetonitrile until a greater than 98% trans/cis ratio is obtained. Recrystallization from isopropanol gives (R*,R*)2-[(dimethylamino)methyl]-1-(3-metboxyphenyl) cyclohexanol hydrochloride free of the nitrile solvent. A hydrochloride of Tramadol can be synthesized without increasing a ratio of trans:cis by including a step in which HCl is added to Tramadol base in the presence of toluene.

16 Claims, 1 Drawing Sheet

SCHEME I
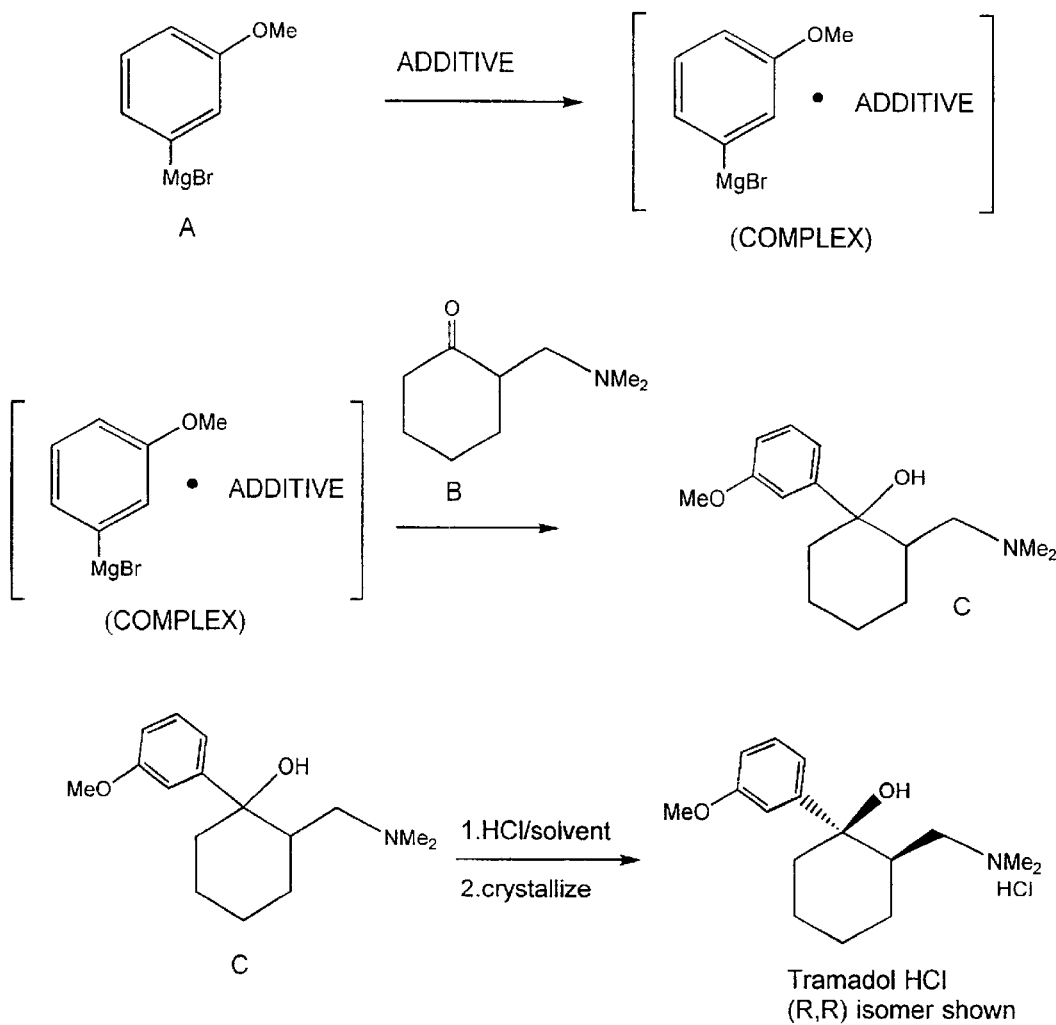

SYNTHESIS AND PURIFICATION OF (R*, R*)-2-[ (DIMETHYLAMINO) METHYL]-1-(3-METHOXYPHENYL) CYCLOHEXANOL HYDROCHLORIDE

This Application is a 317 of PCT/US99/11336 filed May 20, 1999 which claims benefit of Provisional No. 60/086,498 filed May 22, 1998.

BACKGROUND OF THE INVENTION

The compound (R*,R*)-2-[(dimethylamino)methyl]-1-(3-methoxyphenyl)cyclohexanol hydrochloride is a nonaddictive analgesic and is also known as Tramadol. This compound is manufactured by Gruenenthal GmbH of Germany and is sold under tradenames Tramal and Crispin. Methods for the synthesis of Tramadol are described in U.S. Pat. No. 3,652,589 which is incorporated herein by reference. This synthesis leads to a mixture of trans and cis forms of the compound, herein referred to as the trans and cis forms of Tramadol (although the name Tramadol, when used alone, generally refers to substantially pure trans form of the compound). There is some confusion within the literature as to what should be called cis and what should be called trans. For purposes of this disclosure, what is referred to herein as the trans form of Tramadol includes the R,R and S,S isomers as shown by the following two structures:

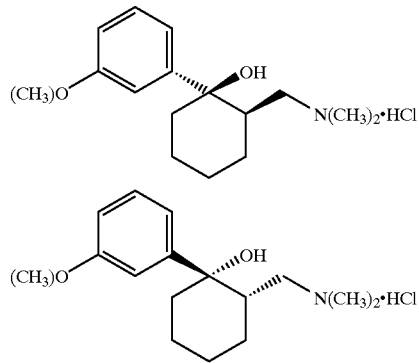

The cis form of Tramadol, as that phrase is used herein, includes the S,R and the R,S isomers which are shown by the following two structures:

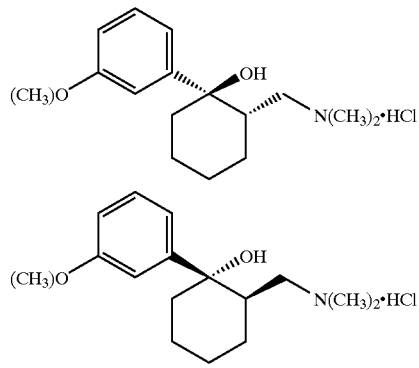

Methods of manufacture begin with a Grignard reaction which results in a mixture of cis and trans isomers. These are then separated by methods taught in the prior art. U.S. Pat. No. 5,652,589 teaches a method of heating the mixture under reflux with a mixture of anhydrous dioxane and water for one hour while stirring and filtering. The filter residue obtained includes the trans form of the hydrochloride of Tramadol. The filtrate is a mixture of about 20–30% cis form and 70–80% trans form. This filtrate can be further separated by cooling to yield crystals which are then pulverized and stirred with dichloromethane at room temperature. The cis isomer is not dissolved whereas the trans isomer goes into solution. This solution is filtered. The filtrate yields substantially pure trans isomer. The filter residue is dissolved in methanol and crystallized by adding ether. The resulting crystals are substantially pure cis isomer of Tramadol.

U.S. Pat. No. 5,414,129, which is incorporated herein by reference, teaches a process for the improved purification and separation of the cis and trans isomers of Tramadol. This '129 patent lists the many problems with using dioxane in the preparation of a compound which is to be used as part of a drug. Included in this list are the following: dioxane has been listed as a category I carcinogen by OSHA (Kirk & Othmer, 3rd edition vol. 9, page 386) and it causes CNS depression and necrosis of the liver and kidneys (Kirk & Othmer, 3rd edition vol. 13, page 267). Therefore, the presence of dioxane as a residue is monitored and a limit of several parts per billion has been set. The '129 patent teaches a method which avoids the use of dioxane. Tramadol is first synthesized via a Grignard reaction to yield a mixture of cis and trans forms plus Grignard reaction side products. This mix of products is combined with a solution of hydrochloric acid in a low molecular weight alcohol or with gaseous hydrogen chloride in the presence of an organic solvent selected from medium molecular weight alcohols, ketones, esters and ethers or aromatic ethers, to effect the selective precipitation of the trans isomer (Tramadol). The '129 patent states that alternative solvents to dioxane which will effectively separate the cis and trans isomers were very hard to find, but those listed in the patent were found to be usable.

BRIEF SUMMARY OF THE INVENTION

In accordance with the present invention, a method is provided for forming a product comprising (R*,R*)-2-[(dimethylamino)methyl]-1-(3-methoxyphenyl) cyclohexanol (Tramadol) by a process selected from the group consisting of 1) synthesizing Tramadol in a sequence of steps including a Grignard reaction in the presence of an additive wherein the presence of said additive results in a higher trans:cis ratio of Tramadol than is obtained in the absence of said additive, 2) synthesizing a hydrochloride of Tramadol without increasing a ratio of trans:cis by performing a step consisting essentially of adding HCl to Tramadol base in the presence of toluene, and 3) synthesizing a hydrochloride of Tramadol while increasing a ratio of trans:cis by converting trans and cis forms of Tramadol to hydrochloride forms and recrystallizing said hydrochloride forms from a nitrile solvent.

BRIEF DESCRIPTION OF THE DRAWING

Scheme 1 shows a scheme for the synthesis of Tramadol in accordance with the invention.

DETAILED DESCRIPTION OF THE INVENTION

According to one embodiment, the instant invention is an improved method for the synthesis and purification of (R*, R*)-2-[(dimethylamino)methyl]-1-(3-methoxyphenyl) cyclohexanol hydrochloride. This method yields an improved trans/cis ratio. The Tramadol base is synthesized in the presence of an additive which may be an amine, an ether such as diglyme, or the like. The base can be converted to its hydrochloride form and then recrystallized from a low molecular weight nitrile such as acetonitrile or propionitrile until a greater than 98% trans/cis ratio is obtained. This then may be finally recrystallized from isopropanol to yield the trans isomer substantially free of the nitrile solvent. This embodiment, utilizing an additive and a new crystallization solvent, avoids the use of dioxane and produces a very high trans/cis product.

The method described herein is an improvement from the earlier work described in U.S. Pat. No. 5,652,589 for which the method yielded a Grignard product that is 78–82% trans. Performing the Grignard reaction in the presence of an additive gives 85–92% trans product. The amine and ether additives are believed to complex with the Grignard reagent, e.g., TDA-1 [tris(2-(2-methoxyethoxy)ethylamine] complexes with some Grignard reagents (Boudin et al., *Tetrahedron* 45:171–180 (1989), incorporated herein by reference). The complex is shown in brackets in Scheme 1. The Grignard can be run in the normal solvents, diethyl ether or THF (tetrahydrofuran), or a mixture of THF and another solvent such as tBuOMe (t-butylmethoxyether) or toluene. The product can be converted to a hydrochloride by conventional means (ether, HCl, or ethanolic HCl with ether), or in THF or in acetonitrile (with or without toluene present). In the last case, solvent does not need to be rigorously removed from the crude hydrochloride to recrystallize. The crude hydrochloride may then be recrystallized from acetonitrile to give >98% trans isomer. A second recrystallization from acetonitrile can give 99.9% trans product. Recrystallization from isopropanol can be performed to remove residual acetonitrile.

In accordance with one embodiment, the process comprises two parts: (1) running the Grignard reaction in the presence of an additive and (2) the use of a new recrystallization solvent as compared to the recrystallization steps of the prior art. This use of the additive in the Grignard reaction improves the yield of the trans product.

One aspect of the invention (shown as Example 6 below), demonstrates that with a carefully controlled concentration of amine and hydrogen chloride in acetonitrile, purification to a better trans/cis mixture occurs in the hydrochloride formation step. This added modification reduces the number of recrystallizations needed by one, as compared to Example 8.

For the Examples below, assays were performed to determine the trans/cis ratio of the purified product. The method for performing these assays was the following HPLC method: A Phenomenex Prodigy 5, C8, 250×4.6 mm column was utilized with detection set at 272 nm. The buffer for running the column was: 25 nM $KH_2PO_4$, adjusted to pH 3.4 with HPLC grade 85% $H_3PO_4$ (phosphate buffer). Mobile phase A consisted of the phosphate buffer 90%:acetonitrile 10%. Mobile phase B consisted of the phosphate buffer 80%:acetonitrile 20%. The column and buffer gradient were run as follows: hold at 100% mobile phase A for 3 minutes, then 0–75% mobile phase B linearly over 20 minutes. Hold at 75% mobile phase B for 7 minutes, then return to 100% mobile phase A over 0.1 minute. Reequilibrate the column for 9.9 minutes with 100% mobile phase A. The flow rate used is 1.5 mL/minute and the column is kept at 45° C. The cis isomers elute first (at 11.2 minutes) and the trans (RS,RS) isomers elute last (12.1 minutes).

A general scheme for the synthesis of Tramadol is shown in the FIGURE. As shown from the FIGURE, 3-bromoanisole is subjected to a Grignard reaction with magnesium and tetrahydrofuran (THF) in the presence of an additive, such as 1-methylimidazole or another of the additives outlined in the Examples below, to form a Grignard reaction product. The additive results in a better trans:cis ratio of Tramadol. The Grignard reaction product is reacted with the Mannich base B, which can be produced by the known Mannich reaction, see, e.g., K. Flick, E. Frankus and E. Friderichs, *Arzneim-Forsch*, 28(1):107–113 (1978) and C. Mannich and R. Braun, *Chem. Berichte*, 53:1874–1876 (1920). The resulting product can be processed as described herein to produce Tramadol having a higher trans:cis ratio.

Specific schemes of the synthesis and purification of Tramadol are given in the following Examples in which different additives are utilized. The first several Examples illustrate the use of additives to the Grignard reaction to increase the trans:cis ratio and the later Examples illustrate recrystallization methods to further improve the trans:cis ratio. These Examples are offered by way of illustration and are not intended to limit the invention in any manner. Standard techniques well known in the art or the techniques specifically described herein are utilized.

EXAMPLE 1

Synthesis of Tramadol Base in the Presence of the Additive TDA-1

To Mg turnings (5.8 g, 0.239 mole) in 70 mL of THF was added (with mechanical stirring) 42.5 g (0.227 mole, 1.5 equivalents) of 3-bromoanisole in 5 mL THF (including wash), adding about ⅕ of it initially and the rest over a 25 minute period after the exothermic reaction started. The mixture was refluxed for one hour further. It was allowed to cool to 42° C. and TDA-1 [tris(2-(2-methoxyethoxy) ethylamine, 95%] (36.5 g, 0.113 mole) was added, followed by 5 mL THF wash. The Mannich base, 23.5 g (0.151 mole) in dry tBuOMe, was added over 10 minutes, which gave a temperature rise from 32 to 67 degrees C. This was refluxed for 1.5 hours, then cooled in an ice-water-bath to 16° C. and quenched with 70 mL (0.28 mole) of 4 M ammonium chloride solution. At one point the pot temperature went to a maximum of 43 degrees. At 17 degrees, 120 mL of 4 M HCl was added, and resulted in a clear solution. To this was added 100 mL of heptane and the mixture filtered to remove a small amount of magnesium. After adding 5 ml more of 4 M HCl, to pH 1.4, the layers were separated. The heptane layer was discarded. The aqueous layer was covered with 150 mL of heptane and taken to pH 9.3 with concentrated ammonium hydroxide. The layers were separated and the aqueous layer was extracted with another 2×100 mL heptane. The combined heptanes were washed with 2×100 mL water. The heptane was dried with magnesium sulfate (10 g) and concentrated to 28.68 g of an oil (72%) that had very little solvent as detected by NMR. HPLC showed an 89/11 mixture of trans/cis products. This 89% trans Tramadol production is an improvement over the 78–82% trans production of the prior art.

EXAMPLE 2

Synthesis of Tramadol in the Presence of the Additive 1-methylimidazole

The Mannich reaction was run to give Mannich hydrochloride in water. This was adjusted to pH 10.8 and extracted with toluene and then dried with magnesium sulfate. A 200 mL solution containing 98 g of the Mannich base B in toluene was thus obtained.

To 24 g of magnesium turnings under 425 mL of dry THF was added 177 g of meta-bromoanisole at such a rate as to keep the reaction at reflux. After the addition, reflux was continued for one hour. At a temperature of 60° C., 77 o of 1-methylimidazole was added. A precipitate formed. The mixture was stirred until all of the precipitate dissolved. The temperature was allowed to fall to 28° C., and then the solution of Mannich base B in toluene (above) was added over 15 min, while a temperature rise to 60° C. was observed. During 2 hours, the reaction mixture was stirred and allowed to cool to room temperature. The mixture was cooled to 15° C. and 420 mL of 4 M ammonium chloride in water was slowly added, keeping the temperature under 30° C. To the mixture was added 350 mL of water. The mixture was cooled while 215 mL of concentrated hydrochloric acid was added, giving a pH of 1.0. The top, organic layer was separated and discarded. The aqueous layer was washed with 150 mL toluene and the toluene discarded. The aqueous mixture was cooled in an ice bath and taken to pH 9.5 with 355 mL of concentrated ammonium hydroxide. The mixture was extracted with 140 mL of toluene. The two phase mixture was filtered before separation to remove insolubles. The aqueous layer was extracted with a second 140 mL of toluene, and the toluene extracts were combined. Small amounts of toluene were added for transfer. Approximately 90 mL of toluene was distilled out to remove water. The toluene solution was assayed to show there is 106 g of a mixture of trans/cis isomers of C there, in a 90.3/9.7 ratio (HPLC). A simple assay of the solution is to remove solvent from a few milliliters of sample by rotary evaporation followed by drying in high vacuum. The solution can be used as such in Example 8 type experiments, or concentrated further. An additional extraction of the original aqueous layer with toluene gave 5.4 g more of the desired product.

As in Example 1, it is seen that the presence of the additive led to an improved trans:cis ratio as compared to the methods of the prior art which do not include the use of additives in the Grignard reaction. For further purification, the product is converted to hydrochloride and recrystallized from acetonitrile as in Example 5 or it can be used as in Example 8 by adding back some toluene.

EXAMPLE 3

Synthesis of Tramadol in the Presence of the Additive Diglyme

To 1.88 g magnesium under 15 mL of dry THF was slowly added 14.5 g of m-bromoanisole in 2 mL of THF. At the end, the mixture was refluxed for 40 minutes more. Then 20 mL of dry 2-methoxyethyl ether (diglyme) was added, and the resulting precipitate stirred until all dissolved. The Mannich base B, 6.0 g in 3 mL THF, was added 15 minutes later. The temperature went to 62° C. and was kept at 60–80° C. for 30 minutes further. The mixture was quenched with 4 M ammonium chloride and worked up as in Example 1. The heptane extract was washed with water and concentrated to give 5.9 g of an oil C, shown to be 88.2/11.8 trans/cis by HPLC. As in Examples 1 and 2 above, the presence of the additive in the Grignard reaction results in improved yields of the trans form of Tramadol.

EXAMPLE 4

Amine and Ether Additives in the Grignard

A variety of amine additives as well as one ether additive were tested in the Grignard reaction. These are set out in the following Table. The use of a few of these additives (TDA-1, 1-methylimidazole, and diglyme) were already noted in Examples 1, 2 and 3, respectively. Also shown are two examples of results from reactions run according to the literature procedure (U.S. Pat. No. 5,652,589) in which no additive was used. For the TDA-1 of Example 1, 2 equivalents of Grignard were used and the TDA-1 is the amount in the experimental. In the remaining Examples, 1.5–1.6 equivalents of Grignard were used and one mole of amine to one mole of Grignard added.

Table of Amine and Ether Additives in the Grignard and Ratios of Products

| Additive | Example No. | Trans/Cis of C | Yield of C |
|---|---|---|---|
| none | literature procedure | 78/22 | 74% |
| none | literature procedure | 81/19 | 74% |
| TDA-1 | 1 | 89/11 | 72% |
| 1-Methylimidazole | 2 | 90.3/9.7 | 67% |
| Diglyme (not an amine) | 3 | 88.2/11.8 | 58% |
| 4-Methylmorpholine | | 82/18 | 65% |
| Diazabicyclo (5.4.0) undec-7-ene | | 89/11 | 35% |
| Triethylamine | | 82/18 | 57% |
| N,N,N',N',N''-Pentamethyldiethylenetriamine | | 90.5/9.5 | 29% |
| Pyridine | | 88/12 | 32% |
| 1,2-Dimethylimnidazole | | 89/11 | 72% |
| 1-Methylpyrrolidine | | 90.6/9.4 | 12% |
| 1,4-Dimethylpiperazine | | 86.5/13.5 | 41% |
| Pyrazine | | 89/11 | 24% |
| S-(−)-nicotine | | 87/13 | 71% |
| 1-Methylpyrrole | | 84.7/15.3 | 38% |
| 4-Methoxypyridine | | 87.6/12.4 | 41% |
| Quinoline | | 88.6/11.4 | 24% |
| 1,5-Diazabicyclo[4.3.0]non-5-ene, (DBN) | | 90.4/9.6 | 44.4% |
| 1-Benzylimidazole | | 89.5/10.5 | 55% |
| 1-Butylimidazole | | 90/10 | 75% |

As seen in the above examples, the additive has an effect on the trans/cis ratio. The prior art examples yielded a ratio of 78/22 or 81/19. The present procedure in the presence of the additives yields ratios from a low of 82/18 to a high of 90.6/9.4. Some of the additives have only a minimal effect on the ratio (for example yielding only an 82/18 ratio), but others have a dramatic effect. For example, a product with an approximately 90/10 ratio has only about one-half the amount of the undesired cis product as compared to the prior art methods. The result of a higher ratio means that fewer crystallization steps may need to be performed.

EXAMPLE 5

Further Purification of Tramadol by Recrystallization of the Hydrochloride from Acetonitrile The 28.04 g (107 millimoles) of oil remaining from Example 1 was converted to the hydrochloride by standard methods, e.g., as in U.S. Pat. No. 3,652,589. The product was air dried to give 28.7 g of the hydrochloride as a white solid (89% for this step). HPLC indicated a 91/9 ratio of trans/cis. Of this, 28.53 g was recrystallized from 255 mL acetonitrile (8.5–9 mL per g of compound) with mechanical stirring (also on cooling) to give 18.8 g. A second recrystallization from 170 mL of acetonitrile gave 16.49 g. The final recrystallization from 62 mL isopropanol (use about 3.8 mL/g of compound) gave 13.39 g. HPLC indicated a 99.99/0.01 ratio of trans/cis. It is seen that recrystallization from acetonitrile results in an improved trans:cis ratio as compared to the initial ratio formed in the making of the base.

Here the beginning product (the Tramadol base C produced in Example 1) had a trans:cis ratio of 89:11 whereas after converting to the hydrochloride followed by 3 rounds of crystallization from acetonitrile the ratio had been improved to 99.99:0.01.

EXAMPLE 6

Production of the Hydrochloride in Acetonitrile and Crystallization Therefrom

It has been found that the most favored method is to prepare the hydrochloride using 1.2–1.3 equivalents of HCl in acetonitrile, crystallize, perform a second crystallization from acetonitrile, and finally crystallize from isopropanol to remove traces of acetonitrile. A sample of the dry toluene solution of Grignard product C from Example 2 was concentrated on a rotary evaporator to 18 g. Examination of the sample showed that it contained 15.5 g of amine, the rest being toluene (2.5 g). The sample was stirred in 120 mL of acetonitrile and a solution of 2.6 g of HCl in acetonitrile (29 mL of solution) was added. The temperature was allowed to rise to 42° C., and then to cool. At 29° C. a precipitate started to form. The mixture was stirred 1.5 h further and then filtered at 23° C., followed by a 15 mL acetonitrile wash. Drying in vacuo yielded 12.9 g of the hydrochloride, 99.3/0.7 trans to cis.

EXAMPLE 7

Preparation of Tramadol Hydrochloride from Crude Tramadol Base (Grignard Product)

Hydrogen chloride gas was bubbled through 40 mL of ice-cooled dry acetonitrile. The weight went up 3.7 g and the volume was measured to be 43 mL. Of this, 40 mL (which has 3.44 g HCl; 94.5 millimoles) was used below. Tramadol base C, 15.4 g and containing 89.8/10.2 trans/cis isomers, was dissolved in 105 mL of dry acetonitrile. The 40 mL above was added in 10 mL increments and the temperature went up to 35° C. from 18° C. After 1 hour, the mixture was cooled to 20° C. and filtered and washed with 10 mL acetonitrile. After drying 11.6 g was obtained (67% yield) which was greater than 98% trans.

EXAMPLE 8

Hydrochloride Formed without Improvement of the Trans:Cis Ratio

Whether a recrystallization step improves the trans:cis ratio of Tramadol depends upon the solvent composition from which the recrystallization is performed. When the hydrochloride form of Tramadol is produced and then crystallized in the presence of a solvent with a high toluene concentration, the ratio of trans:cis remains essentially unchanged. This is in contrast to the recrystallization from a solvent which has a high acetonitrile concentration as was the case in Examples 5–7.

A 21 mL solution of 1.8 g of HCl gas (bubbled at 5° C.) in acetonitrile (yielding a 2.0 M solution), was added to 10.2 g of Grignard product C (90/10 of trans/cis) in 30 mL of toluene and stirred mechanically for 3 hours. The mixture was filtered and washed with toluene. Drying in vacuo yielded 11.2 g (96% recovery). The resulting hydrochloride had a trans/cis ratio of 92:8, essentially the same trans:cis ratio as did the 10.2 g of Grignard product C.

Recrystallization from 90 mL of acetonitrile yielded 8.83 g, which was 96.6/3.4 of trans/cis by HPLC. Of this, 8.6 g was recrystallized from 75 mL of acetonitrile to give 7.44 g, trans/cis ratio of 99.6/0.4.

This example shows that the formation of the hydrochloride in the presence of a relatively large amount of toluene (here about 60%) and crystallization from toluene-acetonitrile does not improve the trans:cis ratio. As the percentage of toluene present in the mixture of toluene and acetonitrile in a crystallization step is decreased, the trans:cis ratio of the recovered product will increase. Steps in which the hydrochloride is recrystallized from acetonitrile do yield an improved trans:cis ratio.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for forming a product comprising (R*,R*)-2-[(dimethylamino)methyl]-1-(3-methoxyphenyl)cyclohexanol (Tramadol) hydrochloride by a process comprising synthesizing Tramadol in a sequence of steps including a Grignard reaction, wherein said Grignard reaction is carried out in the presence of an additive wherein the presence of said additive results in a higher trans:cis ratio of Tramadol than is obtained in the absence of said additive, and converting the resulting base to its hydrochloride form, followed by a step selected from the group consisting of:
   1) synthesizing a hydrochloride of Tramadol, without increasing the ratio of trans:cis, by performing a step of adding HCl to Tramadol base in the presence of toluene; and
   2) synthesizing a hydrochloride of Tramadol while increasing the ratio of trans:cis by converting trans and cis forms of Tramadol to hydrochloride forms and recrystallizing said hydrochloride forms from a nitrile solvent.

2. The method of claim 1 wherein said additive is an amine.

3. The method of claim 2 wherein a nitrogen atom of said amine is part of a heterocyclic ring.

4. The method of claim 2 wherein said amine is a tertiary amine.

5. The method of claim 2 wherein said amine is selected from the group consisting of: tris(2-(2-methoxyethoxy)ethylamine), 1-methyl imidazole, 4-methylmorpholine, diazabicyclo[5.4.0]undec-7-ene, triethylamine, N,N,N',N',N"-pentamethyldiethylenetriamine, pyridine, 1,2-dimethylimidazole, 1-methylpyrrolidine, 1,4-dimethylpiperazine, pyrazine, S-(-)-nicotine, 1-methylpyrrole, 4-methoxypyridine, quinoline, 1,5-diazabicyclo[4.3.0]non-5-ene, 1-benzylimidazole and 1-butylimidazole.

6. The method of claim 1 wherein said additive is an ether.

7. The method of claim 6 wherein said ether is a polyether.

8. The method of claim 6 wherein said ether is diglyme.

9. The method of claim 1 wherein said Grignard reaction is performed in a solvent comprising one or more compounds selected from the group consisting of diethyl ether, tetrahydrofuran, toluene and t-butylmethylether.

10. The method of claim 1 wherein said nitrile solvent is a low molecular weight nitrile solvent.

11. The method of claim 1 wherein said nitrile solvent is acetonitrile.

12. The method of claim 1 wherein said nitrile solvent is utilized, further comprising a step of recrystallizing of Tramadol from isopropanol.

13. The method of claim 1 wherein said toluene is present at a concentration of at least 60%.

14. The method of claim 1 wherein said toluene is present, and wherein a low molecular weight nitrile cosolvent is present in an amount less than said toluene.

15. The method of claim 1 wherein in said Grignard reaction, 3-bromoanisole is converted into a Grignard reaction product.

16. In a method of converting 3-bromoanisole in a Grignard reaction to a Grignard reaction product, the improvement comprising carrying out said Grignard reaction is the presence of an additive selected from the group consisting of 1) an amine selected from the group consisting of: tris(2-(2-methoxyethoxy)ethylamine), 1-methyl imidazole, 4-methylmorpholine, diazabicyclo[5.4.0]undec-7-ene, triethylamine, N,N,N',N',N"-pentamethyldiethylenetriamine, pyridine, 1,2-dimethylimidazole, 1-methylpyrrolidine, 1,4-dimethylpiperazine, pyrazine, S-(−)-nicotine, 1-methylpyrrole, 4-methoxypyridine, quinoline, 1,5-diazabicyclo[4.3.0]non-5-ene, 1-benzylimidazole and 1-butylimidazole and 2) an ether selected from the group consisting of polyethers and diglymes.

\* \* \* \* \*